United States Patent
Merz et al.

[11] Patent Number: 5,369,981
[45] Date of Patent: Dec. 6, 1994

[54] PROCESS FOR CONTINUOUSLY DETERMINING THE DUST CONTENT IN AN EXHAUST GAS FLOW

[75] Inventors: Albert Merz, Karlsruhe; Roland Walter, Graben-Neudorf; Ernst Becker, Korb; Thomas Brielmaier, Blaustein, all of Germany

[73] Assignee: Kernforschungszentrum Karlsruhe GmbH, Karlsruhe, Germany

[21] Appl. No.: 133,066

[22] PCT Filed: May 2, 1992

[86] PCT No.: PCT/DE92/00359

§ 371 Date: Oct. 12, 1993

§ 102(e) Date: Oct. 12, 1993

[87] PCT Pub. No.: WO92/21013

PCT Pub. Date: Nov. 26, 1992

[30] Foreign Application Priority Data

May 10, 1991 [DE] Germany .................. 4115212

[51] Int. Cl.⁵ .................. G01N 15/06; G01N 1/24
[52] U.S. Cl. .................. 73/28.01; 73/23.33; 73/863.23
[58] Field of Search .................. 73/28.01, 28.03, 23.33, 73/863.23, 863.02, 863.03

[56] References Cited

U.S. PATENT DOCUMENTS

| 3,965,748 | 6/1976 | Boubel et al. ............ 73/28.01 X |
| 4,154,088 | 5/1979 | Werner .................. 73/28.01 |
| 4,442,699 | 4/1984 | Ramelot ................. 73/28.01 |
| 4,633,706 | 6/1987 | Ito et al. ............... 73/23.33 |
| 4,856,352 | 8/1989 | Daum et al. ............. 73/863.23 X |
| 5,090,257 | 2/1992 | Bruce ................... 73/863.23 X |

FOREIGN PATENT DOCUMENTS

| 0390942 | 10/1990 | European Pat. Off. ...... 73/28.01 |
| 297902  | 1/1992  | Germany ................. 73/28.01 |

Primary Examiner—Hezron E. Williams
Assistant Examiner—Joseph W. Roskos
Attorney, Agent, or Firm—Klaus J. Bach

[57] ABSTRACT

The invention relates to a process for the continuous determination of the dust content of flowing media with the isokinetic flow sampling with the separation of the dust or aerosols by cake filtration on a filter and the measurement of the pressure drop at the filter to determine its degree of clogging. To this end the time cycle of the quantity of dust separated on the filter is determined by the measurement of the pressure loss at the filter of an isokinetically operating sampling system. To find the dust load, this quantity of dust is related to the partial quantity of gas extracted isokinetically during the period concerned.

4 Claims, 1 Drawing Sheet

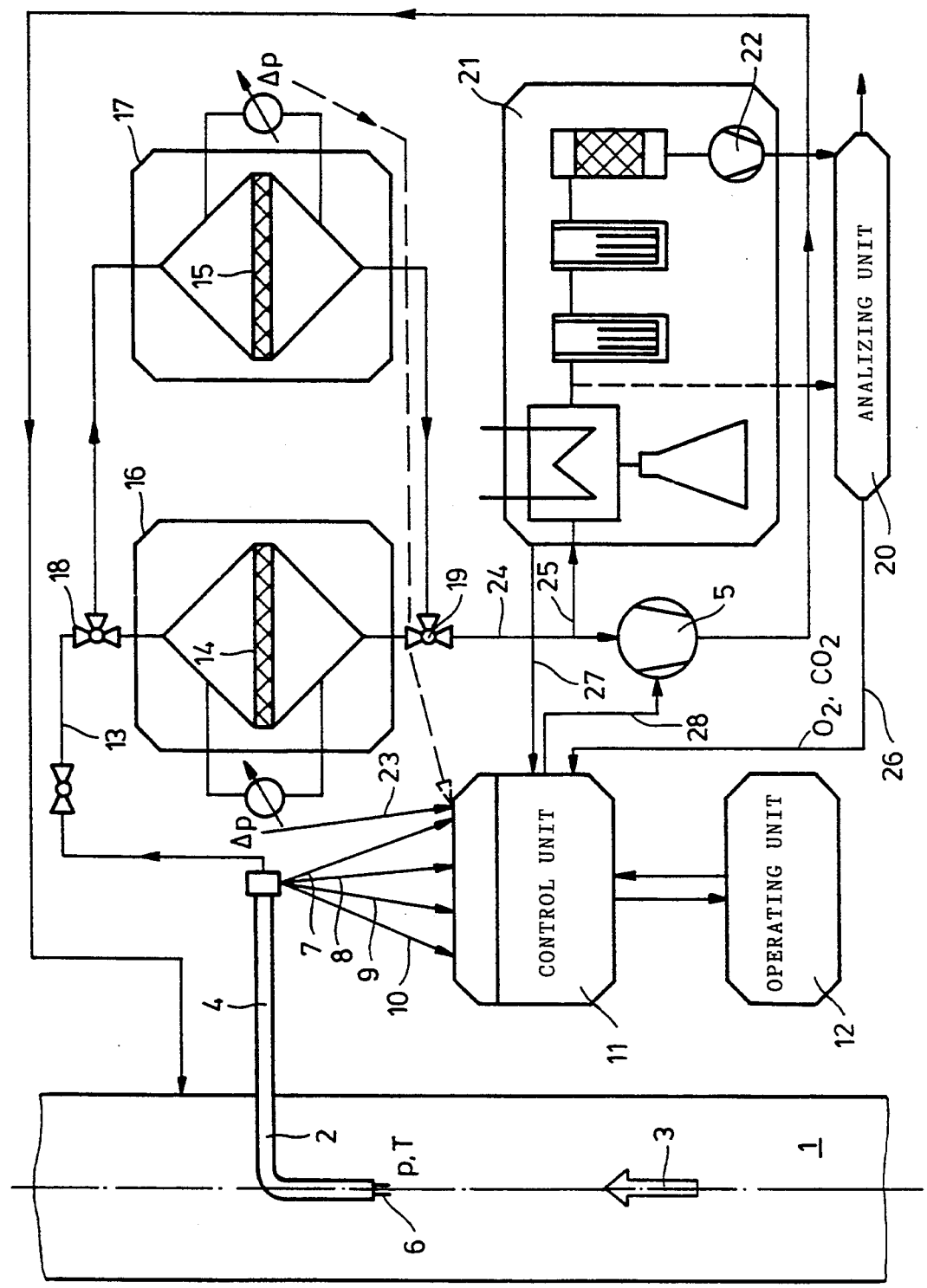

PROCESS FOR CONTINUOUSLY DETERMINING THE DUST CONTENT IN AN EXHAUST GAS FLOW

BACKGROUND OF THE INVENTION

The present invention relates to a process for the continuous determination of the dust content of flowing media with the isokinetic partial flow removal for sampling by separation of the dust or aerosols via cake filtration on a filter.

Known processes for the continuous emission surveillance employ absorption of light waves or other radiation sources. It is also known to monitor the pressure losses in filters for a threshold value at which it is pressurized that the filter needs to be exchanged. Only afterward the integral amount of the particles deposited on the filter can be determined by weight measurements. A continuous surveillance of the amounts deposited over predetermined time steps is not possible with this method.

It is the object of the present invention to provide a process by which the continuous surveillance of dust emissions with subsequent record keeping capability of the sample material regarding the analytical determination of dust content materials such as heavy metals, dioxines, etc. is made possible.

SUMMARY OF THE INVENTION

The invention relates to a process for the continuous determination of the dust content of flowing media with the isokinetic flow sampling with the separation of the dust or aerosols by cake filtration on a filter and the measurement of the pressure drop at the filter to determine its degree of clogging. To this end the time cycle of the quantity of dust separated on the filter is determined by the measurement of the pressure loss at the filter of an isokinetically operating sampling system. To find the dust load, this quantity of dust is related to the partial quantity of gas extracted isokinetically during the period concerned.

The process according to the invention takes into consideration that the pressure loss during filtration depends on the height of the filter cake, the filtration speed, the viscosity of the gases and the properties, such as particle size, particle shape, void volume, etc. of the deposited dust. It further assumes that, during the filtration process, the properties of the deposited materials do not change substantially. Then the increase of the deposited layer and consequently the amount of deposited material can be determined by measuring the pressure loss taking into consideration filter gas speed and viscosity.

Further details of the process according to the invention will be explained below on the basis of a figure.

BRIEF DESCRIPTION OF THE DRAWING

The sole FIGURE is a schematic representation of a measuring arrangement by which the new process can be performed. The process facilitates the continuous determination of dust contents in flowing media with isokinetic partial flow removal for sampling and separation of the dusts or aerosols via cake filtration on a filter and measuring the pressure drop across the filter for determining the degree of filter loading.

In the discharge duct 1 of an environmentally unsafe material emitter there is provided a sampling device, that is, a suction nozzle 2 via which a representative partial stream is removed from the main gas flow 3. The partial stream is removed isokinetically, that is, at the same speed as the main flow, the required vacuum in the suction pipe 4 being generated by a suction pump 5. Isokinetic adjustment of the removal speed of the partial stream at the nozzle opening 6 is done by RPM control of the HF-drive motor of the suction pump 5 via frequency control. An isokinetic control of suction at the nozzle opening 6 requires triple pressure measurements $P_G$ total pressure 7, $ps_T$ static pressure of the partial gas stream 8, $pst_H$ static pressure of the main gas flow 9 and temperature measurement 10 at the nozzle, in order to determine the momentary condition in close proximity of the nozzle opening 6. The pressures are transmitted through slots or passages in the nozzle wall. From these measurement data a measuring and control unit 11 with an operating unit 12 provides the frequency needed for operating the drive motor of the suction pump 5 at the required RPM.

From the suction pipe 4 the gas stream passes through the conduit 13 and, selectively switchably through the filter housings 16 and 17 in which particles are continuously deposited on the microfilters 14 and 15. For continuous long-term or permanent operation the two filters 14 and 15 are therefore provided to which the stream can be selectively switched by control valves 18 and 19.

Downstream of the filters 14 and 15 the discharge conduit 24 includes a by-pass conduit 25 through which a small partial flow is constantly removed and supplied to a wash module 21 in which it is subjected to condensation and adsorption or absorption procedures. In this module 21 soluble harmful gases are absorbed or washed out of the flow.

The partial flow amount is removed by means of a small pump 22 and it is maintained small with regard to the partial gas stream in order to avoid influencing the isokinetic control—that is, changes of the vacuum-removed particle amounts with changing flow conditions in the discharge duct 1.

The filters 14 and 15 and the suctions pump 5 and also the suction pipe 4 are provided with a heater in order to prevent the gas stream temperature from falling below the condensation point and thereby prevent condensation of the harmful gases in the area of particle separation. This is important for a clear distinction between particulate harmful material and harmful gases in the exhaust gas. After particle removal the partial stream discharged from the pump 5 is returned to the duct 1 and the flow from the pump 22 is discharged to the environment.

In the filters 14 and 15 the pressure differential $\Delta P$ is determined from the pressure measured in front of and behind the respective filter and is supplied as control value 23 to the control unit 11. The control values 26, 27 and 28 transmit values for the gas analysis, gas humidity and pump motor control.

With the described measuring arrangement the new process is performed as follows:

First the pressure loss through the filters 14 or 15 before use is determined at the beginning of the filtering process. This is done by placing the filters 14, 15 into the housings 16 and 17. With the first exposure of the filters to the gas stream the pressure loss through the fresh is determined as soon as stable operating conditions are achieved. The filters consist of high-purity quartz fiber filters of normally web-like woven sheets.

Subsequently, the instantaneous pressure loss is measured continuously or at intervals while the isokinetic partial stream sampling conditions are maintained. During the procedure the characteristic values are continuously processed. In this way, the instantaneous pressure loss is continuously measured and its time-dependent changes are taken into account. Finally, the time-dependent change of the amount of dust deposited on a filter is determined therefrom.

Continuous maintenance of the isokinetic condition is, for the depositing of the dust on the filter, basically not essential; maintenance of those conditions is important rather exclusively for the mathematical processing of the measured values.

Further, the corresponding flow parameters, system pressures, system temperature, gas composition with regard to $CO_2$, $O_2$, gas humidity are continuously monitored. This is done, for example, in the wash module 21 and the analyzing unit 20 as well as at the nozzle opening 6, see also the FIGURE. The measured values are continuously supplied to the measuring and control unit 11.

In the control unit the data relating to the gas such as density, viscosity, gas flow volume and Reynolds number are calculated from the data determined in the previous step. These data are needed for further calculations and are continuously recorded.

Further the absolute amount of dust deposited in the filters 14 and 15 and its time-dependent changes are then calculated by means of the filter equation.

This is done utilizing the values obtained in the preceding steps. The filter equation is well known and is based on the flow through particulate material, that is, particle collections deposited on filter surfaces or filter cakes. The calculation has to coincide on a time basis with the determination of the pressure losses and with the calculation of the flow and gas parameters.

Finally the amount of dust collected during a respective period must be brought into relation with the instantaneous partial stream gas flow volume under standard conditions. Then the emission rate can be determined:

$$\frac{\text{Mass}}{\text{Volume}},$$

wherein the volume is based on standard conditions (for example, 1013 mbar pressure, 273° K., humidity 0).

Subsequently, after conclusion of the filtration procedure, there is a gravimetric determination of the amount of dust deposited for comparison with the total calculated amount for the correction of the material constant if there is possibly a deviation.

With a permanent surveillance of dust emissions the average daily emissions and half-hour average values have to be provided. Revision after a monitoring cycle provides, in retrospect, a measure for the quality of the calculated emission rates. With a deviation present a retroactive correction needs to be effected. This may be the case, for example, if the quality of the dust deposited with regard to the flow through the filter has changed, for example, if the particle composition has changed.

The calculating steps may be made in fixed cycles wherein the cycle intervals are in the range of seconds. That means the calculations are continuously periodically repeated with the actual data. The following gives a calculating scheme and the measurement values for an example:

LPS measurement of the dust loading.

The increase of the pressure loss across the filter depends on the filtration speed $v_F$, the filter loading h and the viscosity $\eta$.

The change $\Delta h$ of the filter loading can be calculated therefrom:

$$h = \frac{\Delta P_F}{\eta v_F} \quad h_i = h_{i+1} - h_i \quad h(10^6/m) \tag{1}$$

The pressure loss $\Delta P_F$ is measured, the viscosity $\eta$ is already calculated in the isokinetic control circuit and the filtration speed can be determined from the partial stream speed:

$$v_F = v_T \cdot \frac{d_i^2}{(300 \text{ mm})^2} \quad d_i(\text{mm}) \tag{2}$$

At the beginning of sampling the value $h_o$ is determined as soon as the system has achieved stable operating conditions. (It should be possible to enter the point of time for determining the value $h_o$ variably in system plane 2 and it should be with a base value of $90_s$.)

The values of h should be determined in a seconds cycle and recorded by a recorder via an analog output. Designation: "relative dust loading".

After every 30 minutes the actual value of h is compared with the value determined 30 minutes earlier. The difference $\Delta h_i$ is multiplied by the estimated emission constant $E_a$, whereby an estimated dust volume $\Delta m_{ai}$ is obtained which, with respect to the partial gas volume taken during this period, provides for the estimated dust loading:

$$B_{ai} = \frac{\Delta m_{ai}}{V_{Ti}} \quad B_{ai}(\text{mg}/m_n^3)$$

At the end of the sampling, shortly before the closing of the shut-off valve, the value h is once more determined and recorded.

After completion of the sampling the dust amount is determined by weighing and the value is entered. The actual emission constant is then calculated and the estimated values for the dust loading are corrected.

The actual emission constant $E_\tau$ is calculated on the basis of the total amount of dust and the difference of the values for h between the beginning and the end of the sampling process.

$$E_\tau = \frac{m}{h_{end} - h_o} \quad E_\tau \, (\text{mg} \cdot m/10^6)$$

This value of the emission constant serves as new value $E_a$ for the following sampling procedure. But there must also be the possibility to substitute another value for $E_a$ in system plane 2.

Average half-hour values should be given on the screen as well as on the final report in the form of a bar diagram with maximally 48 values.

| Example: Emission filter TAMARA nozzle $d_i = 16$ mm | | | | | | | |
|---|---|---|---|---|---|---|---|
| t [h] | $\Delta P$ [mbar] | $v_T$ [m/s] | $v_F$ [m/s] | $\eta$ [$10^{-6}$Pas] | h [$10^6$/m] | $\Delta m_a$ [mg] | $\Delta m_r$ [mg] |
| 0 | 4.35 | 10.0 | 0.028 | 20.0 | 777 = $h_o$ | 0 | 0 |
| 0.5 | 4.40 | 9.5 | 0.027 | 20.0 | 815 | 10.72 | 12.04 |

| | | | Example: Emission filter TAMARA nozzle $d_i = 16$ mm | | | | |
|---|---|---|---|---|---|---|---|
| t [h] | ΔP [mbar] | $v_T$ [m/s] | $v_F$ [m/s] | η [$10^{-6}$Pas] | h [$10^6$/m] | $\Delta m_a$ [mg] | $\Delta m_r$ [mg] |
| 1   | 4.80  | 9.5  | 0.027 | 19.8 | 898  | 23.42 | 26.30 |
| 1.5 | 5.30  | 9.8  | 0.028 | 19.8 | 956  | 16.37 | 18.38 |
| 2   | 5.80  | 10.0 | 0.028 | 19.6 | 1057 | 28.50 | 32.0  |
| 2.5 | 6.20  | 9.5  | 0.027 | 19.6 | 1172 | 32.45 | 36.44 |
| 3   | 6.80  | 9.8  | 0.028 | 19.6 | 1239 | 18.91 | 21.24 |
| 3.5 | 7.30  | 10.2 | 0.029 | 19.8 | 1271 | 9.03  | 10.14 |
| 4   | 7.60  | 10.5 | 0.030 | 19.8 | 1279 | 2.26  | 2.54  |
| 4.5 | 7.80  | 9.8  | 0.028 | 20.0 | 1393 | 32.17 | 36.13 |
| 5   | 8.60  | 10.0 | 0.028 | 20.0 | 1536 | 40.35 | 45.32 |
| 20  | 24.20 | 10.0 | 0.028 | 20.0 | 4321 |       |       |

The estimation of the dust content was based on an emission constant $E_a = 0.2822$. Weighing showed a dust amount of 1123 mg, the increase of the value h during the total sampling time was 3544 $10^6$/m. The actual emission constant $E_{real}$ is therefore $$E_T = \frac{m_{ges}}{\Sigma \Delta h_i} = 0.3169 \text{ mg} \cdot \text{m}/10^6$$

The estimated values therefore have to be multiplied by the factor $$\frac{E_T}{E_a}.$$

A substantial advantage of the new process is that, with every particular sampling procedure, the apparatus characteristic can be checked and if necessary corrected by gravimetrically determined values, that is, the classic process for dust content determination. By adjustment of the geometric dimensions of the sampling system the process may be utilized for measuring higher as well as smaller dust contents.

LIST OF REFERENCE NUMERALS

1 Discharge duct
2 Nozzle, suction nozzle
3 Main gas flow
4 Suction pipe
5 Suction pump
6 Nozzle opening
7 Total pressure
8 Static pressure of the partial gas stream $pst_T$
9 Static pressure of the main gas flow $pst_H$
10 Temperature T
11 Measuring and control unit
12 Operating unit
13 Conduit
14 Filter
15 Filter
16 Filter housing
17 Filter housing
18 Control valve
19 Control valve
20 Analyzing unit
21 Wash module
22 Pump
23 Control value
24 Discharge conduit
25 By-pass conduit
26 Control value gas
27 Control value humidity
28 Control value pump motor

What is claimed is:

1. A process for the continuous determination of the dust emission in an exhaust gas containing harmful components by determining the dust content of the exhaust gas with isokinetic partial flow sampling and separation of the dust or aerosols from the exhaust gas by cake filtration on a filter, comprising the following process steps:
    a) determining the pressure loss in the partial flow when passing through a fresh filter at the beginning of a separation process,
    b) continuous further determination of the instantaneous pressure loss while maintaining the isokinetic flow sampling conditions and continuous processing of the characteristic pressure loss values, with consequential determination of the time-dependent change of the amount of dust deposited on the filter,
    c) measuring the respective flow parameters comprising system pressures, system temperature, gas composition including $CO_2$, $O_2$, and gas humidity,
    d) calculation of the gas-relevant data including density, viscosity, volume flow, and Reynolds number from the data determined in step c),
    e) calculation of the absolute dust volume deposited on the filter and its time-dependent change by means of the filter equation at the same time at which steps b), c) and d) are performed, and
    f) assigning the dust amounts deposited in a particular time period to the instantaneous partial sampling flow volume under standard conditions.

2. A process according to claim 1, comprising the following additional step:
    g) gravimetric determination of the deposited amount of dust after completion of the process for comparison with the sum value of the calculation for the correction of the material constant upon presence of a deviation.

3. A process according to claim 1, wherein step b) is performed periodically.

4. A process according to claim 1, comprising the following additional step:
    h) specifying the dust content in the form as required by the emission surveillance authorities, said form comprising, selectively, a continuous signal, average half-hourly, hourly and daily values.

* * * * *